United States Patent [19]
Thornton

[11] Patent Number: 5,311,890
[45] Date of Patent: May 17, 1994

[54] TEETH CLEANING ELEMENT

[76] Inventor: Thomas F. Thornton, 43 Contentment Island Rd., Darien, Conn. 06820

[21] Appl. No.: 26,843

[22] Filed: Mar. 5, 1993

[51] Int. Cl.$^5$ .............................................. A61C 15/00
[52] U.S. Cl. .................................... 132/329; 132/321
[58] Field of Search .............................. 132/321, 329

[56] References Cited

U.S. PATENT DOCUMENTS

| | | | |
|---|---|---|---|
| 3,837,351 | 9/1974 | Thornton | 132/321 |
| 3,896,824 | 7/1975 | Thornton | 132/321 |
| 3,943,949 | 3/1976 | Ashton et al. | 132/321 |
| 4,008,727 | 2/1977 | Thornton | 132/321 |
| 4,080,777 | 3/1978 | Griset, Jr. | 57/208 |
| 4,142,538 | 3/1979 | Thornton | 132/321 |
| 4,265,258 | 5/1981 | Eaton, II | 132/321 |
| 4,832,063 | 5/1989 | Smole | 132/321 |
| 5,094,255 | 3/1992 | Ringle | 132/321 |
| 5,183,063 | 2/1993 | Ringle et al. | 132/321 |

Primary Examiner—Gene Mancene
Assistant Examiner—Frank A. LaViola
Attorney, Agent, or Firm—James J. McKeever

[57] ABSTRACT

A teeth cleaning element containing threading end portions for cleaning relatively large spaces in the teeth consists of from about 400 to about 800 filaments in an elongated bundle that is from about 1,200 to 2,400 about denier. The filaments at the mid-portion of the length of the bundle are textured with the crimps and crinkles of the texturing of the several filaments being intermingled and in contact at numerous points and being adhered together at the contact points to form a bulky, longitudinal, longitudinally and laterally resilient mass. The filaments at the opposite end portions of the bundle that extend from the bulky mid-portion are adhered together in compact, smooth parallel relation.

9 Claims, 1 Drawing Sheet

TEETH CLEANING ELEMENT

BACKGROUND OF THE INVENTION

The present invention is a string like element for cleaning relatively large spaces is teeth, such as the spaces in teeth which include bridges, implants, braces, orthodontic appliances or other types of conditions which may create unusually large spaces in which particles of food and dental plaque may become trapped and which can not be cleared and cleaned effectively with conventional dental floss.

PRIOR ART

In my U.S. Pat. No. 3,896,824 I disclose a string-like teeth cleaner formed of bundled filaments in which the filaments in a portion of the bundle are textured by having been crimped and crinkled and the textured filament portions are adhered together at various contact points to form an elongated, laterally enlarged spongy or resilient portion. The bundled filaments extending from the respective ends of the enlarged, spongy portion are adhered together in tight parallel relation to be slim and smooth, like dental floss, so as to enable it to be pressed down between teeth into the space between the teeth at the gum line. The enlarged spongy portion is intended to more nearly fill the space between teeth at the gum line which is normally larger than the space between adjacent teeth at their crowns. In addition the spongy enlarged portion is longitudinally and laterally resilient so that when it is pulled longitudinally it stretches into a thinner diameter so that it can be introduced into relatively small spaces and then expand slightly to fill that space when the tension is relaesed to let it return to its normal relaxed diameter.

The cleaner of my prior patent, described above, is formed of 200 to 300 filaments and is of small enough diameter for its thin end portions to be inserted into the crevice between teeth as dental floss and for its larger brush portion to fill the spaces ordinarily occurring in teeth. However, it has been found that for cleaning larger spaces as encountered between implants or in braces, for example, my prior cleaner is not too satisfactory. It's brush portion is not large enough to work well in unusually large spaces and it is not rugged enough to withstand being severely stretched, abraded and compressed when used in tight spaces. By using two or three of the prior cleaners together enough bulk can be provided for clearing and cleaning larger spaces, but they still can not stand up to the added abrasion, compression and stretching stresses encountered with bridges, orthodontic appliances and the like. Due to interproximal stresses they seem to stretch and break down in mass relatively quickly when used in such stressful environments and are not ideally suited for such use, even when tripled.

BRIEF SUMMARY OF THE INVENTION

The teeth cleaning element of the present invention is particularly adapted for clearing and cleaning relatively larger spaces than my prior cleaner is adapted for, but perhaps more importantly its particular structure gives it great resistance to being stretched out and deformed when used, as it is particularly adapted to be used, for cleaning in and around bridges, implants and orthodontic appliances which severely stretch out prior cleaners of the string type.

The larger size of the teeth cleaning element of this invention obviously adapt it for cleaning larger spaces, but it was found that making it in a large size by making it of at least 400 individual filaments each of a size to provide a strand of over 1,200 denier, and preferably about 600 fiaments of about 1,800 denier, resulted in a cleaning element whose enlarged, bulky, 'working' portion surprisingly turned out to have more and better utilitarian properties than anticipated. For example in previous experiments to provide a teeth cleaner for the larger spaces encountered when the teeth include implants or orthodontic appliances, such as braces or bridges, two or three of the string type teeth cleaners as discolosed in my above mentioned prior patent were placed side by side and threaded through one of the spaces to provide a larger size 'working' brush portion for cleaning the larger space. However, this combination was not very satisfactory for the purpose. It was not sufficiently resilient to provide effective cleaning action and its filament mass tended to break down after a short period of use under the more severe abrasive and stressful conditions encountered with this type of use. The working filament brush mass tended to break down rendering the working portion ineffective for suitable cleaning action.

A group of eleven participants having either implants, bridges, orthodontic appliances, or periodontal problems were given a choice of cleaning their problem areas with three string type cleaners of the prior art having a combined total of about 600 filaments and 1,800 denier or one cleaner of the present invention having about 600 filaments and 1,800 denier. After using each choice, all eleven particiapants agreed that the filament brush portion of the present invention is greatly superior to the combined brush portions of the prior art cleaners due to the increased effectiveness, durability, and ability to maintain body diameter after repeated passages.

With the cleaning element of the present invention, in which there are at least 400 filaments forming a bundle of about 1,200 denier, all the total number of the textured filaments are intermingled in one bundle in the 'working' portion and are interconnected at many points throughout the working portion. This imparts greater strength and durabiltiy to this working portion than in the working portions of the smaller dimensioned string type cleaners of the prior art. In fact in a cleaning element of this invention the strength, durability, and resilience and elastic memory, which are critical for effective cleaning action, turned out to be exponentially greater than might be expected when 400 or more filaments were combined to form a cleaning element of about 1,200 or more denier. This cleaning element turns out to be particularly well adapted for multiple reuses. It stands up well under repeated wetting, drying and abrasive contact with all types of interproximal cleaning.

DESCRIPTION OF THE DRAWINGS

Further objects, advantages and features of the teeth cleening element of this invention will be apparent from the following detailed description of an illustrative embodiment of the invention shown in the accompanying drawings in which.

DETAILED DESCRIPTION

Figure 1:
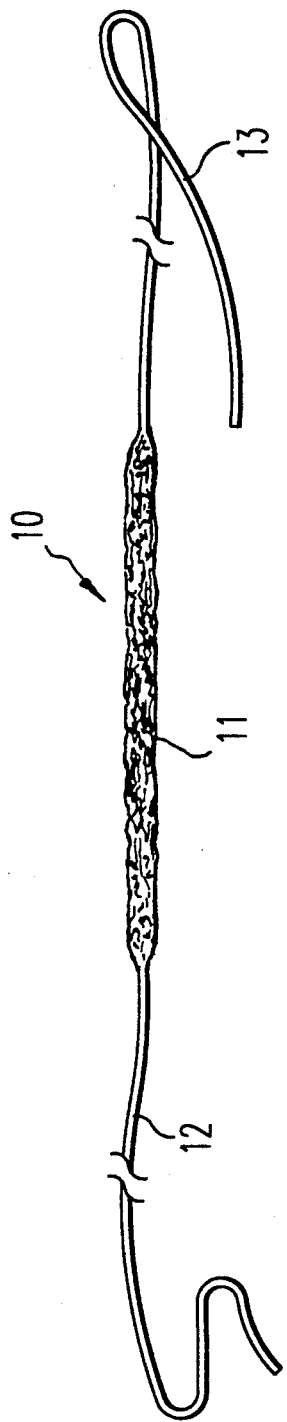
FIG. 1 is a side elevation of a teeth cleaning element of the present invention.

Referring now to FIG. 1 a teeth cleaning element 10 in accordance with the present invention is a strand of filaments with an elongated bulky and spongy mid-portion 11 and smooth, compact string threader like portions 12 and 13 extending therefrom.

The strand that makes up the cleaning element 11 is a yarn consisting of a bundle of at least 400 filaments of a size and weight to make the yarn at least about 1,200 denier. In genera to provide an cleaning element having the desired properties of strength, ruggedness and durability for the cleaning element of this invention there should be from about 400 to about 800 filaments in the bundle comprising the yarn and it should be between about 1,200 and about 2,400 denier. In the preferred form there are 600 filaments and the denier is 1,800.

The yarn used in making a cleaning element of this invention is made up of filaments which are textured. That is, the filaments, which are preferably nylon or polyester and are man made, are initially smooth, but are textured by having crinkles and crimps set in them so that they resemble natural fibers. Textured filaments of this type are disclosed in U.S. Pat. Nos. 2,919,534, 3,077,724 and 3,091912, for example.

Cleaning elements of this invention are manufactured by coating the textured yarn with a synthetic resin, such as polyester or nylon dissolved in alcohol, and drying it. Then an elongated portion of the yarn, in which the crimps and crinkles in the filaments making up the yarn are intermingled and interleafed, is heated so that the synthetic resin coating is dried and adheres the crimps and crinkles of the various filaments together at their points of contact. This provides the bulky resilient portion 11 of the cleaning element.

This portion 11 is the working, brush portion of the cleaner and is laterally and longitudinally resilient as well as being strong and rugged. This is probably due to the many internal interconnections of the filaments in this portion 11.

The end portions 12 and 13 extending out from the bulky 'working' portion 11 are made compact and smooth, This is accomplished by stretching these portions longitudinally to draw out the crimps and crinkles, heating the coating on them to dry it while holding the portions 12 and 13 in stretched condition so that dried coating adheres the filaments in these portions together in smooth parallel condition. These sections 12 and 13 are used to thread the cleaner into various spaces.

Figure 2:
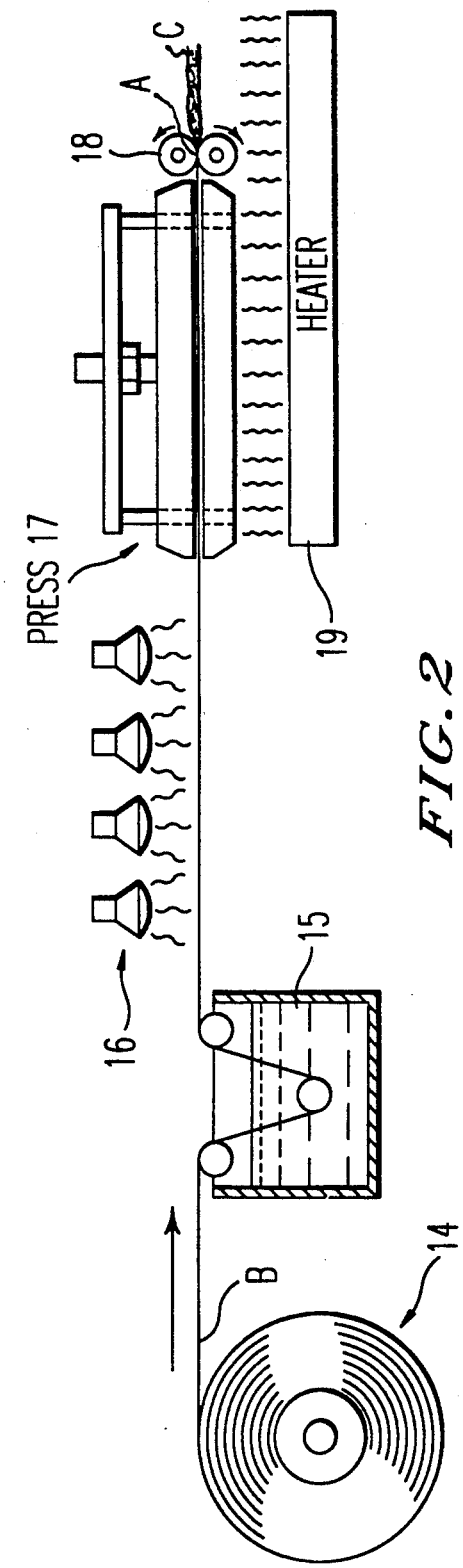
FIG. 2 is a diagramatic view of equipment and a method for making the teeth cleaning element shown in FIG. 1.

FIG. 2 illustrates equipment that could be used for making a cleaning element of the present invention. As shown textured yarn from a spool 14 is drawn through a bath 15 of nylon dissolved in alcohol to coat the yarn. The coating is then dried by lamps 16 as the yarn is drawn past them and through a press 17 to a pair of rolls 18. By braking the spool 14 the section of yarn between the point B at spool 14 and point A at the rolls 18 is stretched to pull out the crimps and crinkles and hold it in straightened condition as the heater 19 heats it to further dry the coating as the press 17 presses it to compact it so that it remains smooth and compact after has thus been dried.

The portion of the yarn to the right of the rolls 18, between points A and C, which becomes the working 'brush' portion 11 of the cleaning element, is not under tension as it is dried so that it remains in its textured condition with its crimps and crinkles fused together at the numerous contact points and thereby provides the rugged, resilient 'brush' portion 11 described above.

In use the smooth, relatively thin end portions 12 and 13 of the cleaner 10 may be used to thread the cleaner through spaces in the teeth that are to be cleared and cleaned and then used as handles for pulling the element back and forth through the various spaces with a seesaw action so that its 'working' brush portion 11 cleans them out. Because of the strength, durability and resilience of the cleaner 10 constructed as described above it can be reused many times without stretching out and becoming deformed.

The present invention has been described and shown in the accompanying drawings with regard to the presently preferred embodiments. It is not intended for this description to be unduly limiting of the present invention which is intended to be defined only by by these means and other obvious equivalents as set forth in the scope of the following attached claims.

What is claimed is:

1. A teeth cleaning element for cleaning relatively large spaces in teeth comprising:
   an elongated bundle from about 400 to about 800 individual filaments in which the filaments in a mid-portion of the length of the bundle are textured by being crimped and crinkled with the crimps and crinkles of the respective filaments being in contact with each other and adhered together at their points of contact, forming a bulky, cohesive, laterally and longitudinally resilient mass of the textured filaments, and in which the filaments in the end portions of the bundle extending outward from the bulky mid-portion are adhered together in compact, smooth, substantially parallel relation, said bundle being of from about 1,200 to about 2,400 denier.

2. The teeth cleaning element of claim 1 in which the bundle is formed of at least about 600 filaments and is about 1,800 denier.

3. The teeth cleaning element of claim 1 wherein the filaments are man made synthetic resins from the group consisting of nylon and polyester.

4. The teeth cleaning element of claim I wherein the filaments are adhered together with a synthetic resin from the group consisting of nylon and polyester.

5. The teeth cleaning element of claim 1 wherein the filaments are nylon and adhered together with a nylon resin.

6. A teeth cleaning element for cleaning relatively large spaces in teeth comprising:
   an elongated bundle of about 600 individual filaments of a synthetic yarn forming a bundle of about 1,800 denier,
   the filaments in a mid-portion of the length of said bundle being textured by being crimped and crinkled,
   said crimps and crinkles of the respective filaments being in contact with each other and adhered together at their points of contact, forming a bulky, cohesive, laterally and longitudinally resilient mass of the textured filaments, and
   the filaments in the end portions of said bundle extending outward from said bulky mid-portion being adhered together in compact, smooth, substantially parallel relation.

7. The cleaning element of claim 6 wherein the filaments are from the group consisting of nylon and polyester.

8. The cleaning element of claim 6 wherein the filaments are adhered together with a synthetic resin from the group consisting of nylon and polyester.

9. The cleaning element of claim 6 wherein the filaments are nylon and adhered together with a nylon resin.

* * * * *